United States Patent [19]

Kim et al.

[11] Patent Number: 4,513,134

[45] Date of Patent: Apr. 23, 1985

[54] METHOD OF PREPARATION OF 3-METHYLENE CEPHAM COMPOUNDS

[75] Inventors: Wan J. Kim; Cheol H. Lee, both of Seoul; Moon H. Lee, Inchon, all of Rep. of Korea

[73] Assignee: Korea Advanced Institute of Science and Technology, Seoul, Rep. of Korea

[21] Appl. No.: 487,421

[22] Filed: Apr. 21, 1983

[30] Foreign Application Priority Data

Feb. 7, 1983 [KR] Rep. of Korea ............... 1983-460

[51] Int. Cl.³ ........................................... C07D 501/02
[52] U.S. Cl. ...................................... 544/16; 544/22; 260/239 A

[58] Field of Search ............... 544/22, 26, 27, 16, 544/21, 28, 25; 424/46

[56] References Cited

U.S. PATENT DOCUMENTS 3,929,775  12/1975  Ochiai et al. ..................... 544/16
4,079,181  3/1978  Tsuji et al. ....................... 544/16

Primary Examiner—Nicholas S. Rizzo
Attorney, Agent, or Firm—Birch, Stewart, Kolasch & Birch

[57] ABSTRACT

A method for the preparation of 3-methylene cepham compounds which comprises reacting 3-halomethyl butenoate derivatives of thiazolinoazetidinone with an aqueous acid solution in a mixed organic solvent.

12 Claims, No Drawings

METHOD OF PREPARATION OF 3-METHYLENE CEPHAM COMPOUNDS

FIELD OF THE INVENTION

This invention relates to a newly improved process for preparing 3-methylene cepham compounds represented in the following formula (I). 3-Methylene cepham compounds are useful reaction intermediates for preparing 3-substituted cephalosporin antibiotics.

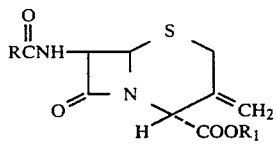
(I)

Wherein;
R is benzyl or phenoxymethyl,
$R_1$ is a carboxylic acid protecting group which can be represented as benzhydryl, p-nitrobenzyl, benzyl, p-methoxybenzyl, 2,2,2-trichloroethyl.

In the process of the present invention, 3-methylene cepham compounds of the formula (I) are prepared by treating 3-halomethyl butenoate derivatives of thiazolinoazetidinone described in the following formula (II) with an aqueous acid solution in a mixed organic solvent.

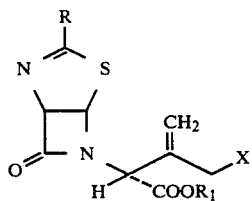
(II)

Wherein:
R is benzyl or phenoxymethyl,
$R_1$ is a carboxylic acid protecting group which can be represented as benzhydryl, p-nitrobenzyl, benzyl, p-methoxybenzyl, 2,2,2-trichloroethyl,
X is chloro, bromo, iodo.

Of the β-lactam antibiotics, cephalosporine derivatives have been used extensively for the treatment of infectious diseases in man because of their wide antibacterial activity and less harmful side effects as compared to penicillins. But existing antibiotics are becoming weak in their activities due to growing bacterial resistances. There has, therefore been considerable research effort directed toward chemical modification of those compounds and toward preparation of new cephalosporin derivatives. Much emphasis has been placed on the variation of the $C_7$-acylamino substituent and now specifically on the variation of the $C_3$-substituent of cepham compounds.

BACKGROUND OF THE INVENTION

3-Methylene cepham compounds of the formula (I) have been known as compounds since 1966 when R. B. Morine found them as a byproduct of a ring expansion reaction of penicillin sulfoxide compounds.

There were reports that those compounds could be used for preparation of 7-aminodeacetoxy cephalosporine acid and its biologically active derivatives, and also for the preparation of 3-methoxy and 3-halocephem compounds. (refer to J. A. Chem. Soc. 95,2994 (1973), J. Am. Chem. Soc. 96,4986 (1974)). 3-Bromomethyl cepham compounds described in the following formula (III) which are useful precursors for various 3-substituted cephalosporine antibiotics can be prepared by bromination of 3-methylene cepham compounds of the formula (I).

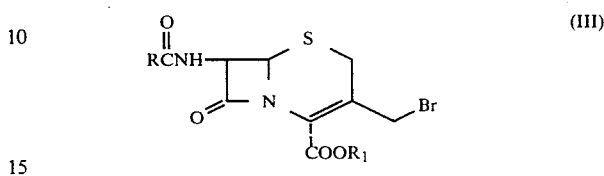
(III)

Wherein
R is benzyl or phenoxymethyl,
$R_1$ is benzhydryl, p-nitrobenzyl, benzyl, p-methoxybenzyl, 2,2,2-trichloroethyl, etc.

There are three known methods of preparation of 3-methylene cepham compounds of the formula (I). In the first method, according to U.S. Pat. No. 4,159,266 (1979. 6. 26) and Korea Pat. No. 80-1399 (1980. 12. 2), 3-methylene cepham sulfoxide compounds are prepared by intramolecular cyclization of penicilline sulfoxide compounds derived through the reaction of sulfinyl chloride, sulfinic acid, sulfinate ester, thiosulfinate ester, sulfinamide, and their sulfinimide derivatives with Friedel-Crafts-catalysts or a metathetic cation forming agent.

The reaction process is represented by the following reaction scheme.

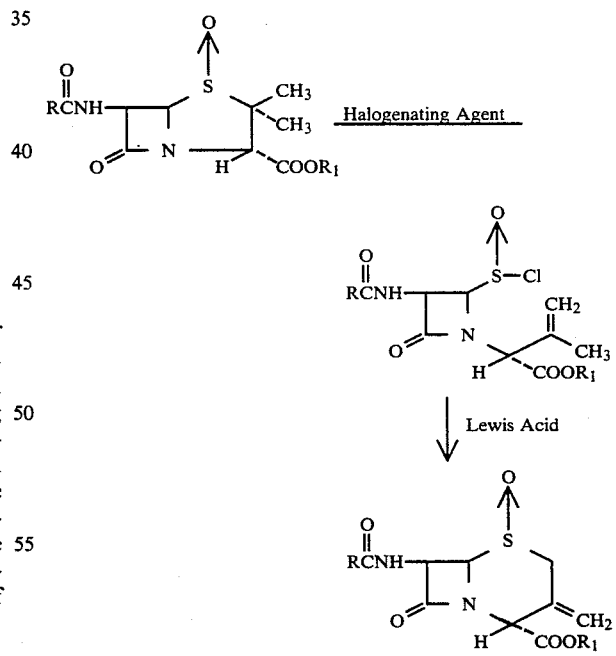

Although this method which employs a sulfinyl chloride intermediate is now most suitable for industrialization, there is a shortcoming in that 3-methylene cepham sulfoxide compounds have to be reduced to obtain 3-methylene cepham compounds of the formula (I).

The second method employs photo-chemical cyclization through a 4-benzothiazolidine dithioazetidinone intermediate (refer to Tetrahedron letter No. 39,3425

(1977)) and is represented by the following reaction scheme.

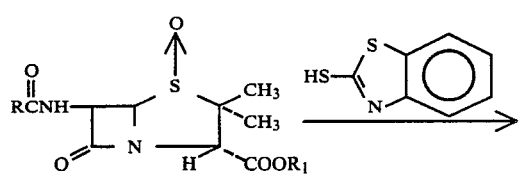

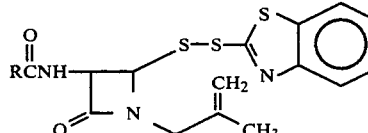

Light (Arc Lamp)
Organic Solvent

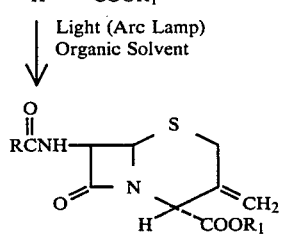

This photo-chemical method is not economical because it needs a dilution step requiring a great amount of solvent in addition, the yield of the reaction is low.

In the third method, 2-halomethylphenam compounds are prepared by the use a 4-benzothiazolidine dithioazetidinone intermediate and 3-halo-3-methylcepham compounds are prepared from 2-halomethylphenam derivatives by the use of dimethyl formamide (D.M.F). 3-halo-3-methyl cepham sulfoxide compounds are obtained by oxidation of 3-halo-3-methyl cepham compounds. Also 3-methylene cepham sulfoxide compounds are obtained by Dehydrobromination of 3-halo-3-methylcepham sulfoxide compounds. (refer to Tetrahedron letter No. 32,3001 (1973), GB 2,013,673A (1979. 8. 15), J. Org. Chem. Vol. 42, No. 17, 2887 (1977), Tetrahedron letter No. 32,2915 (1978)).

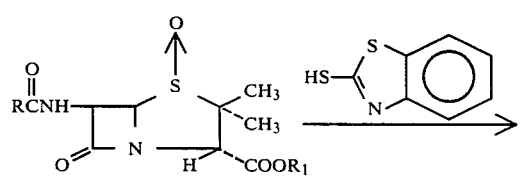

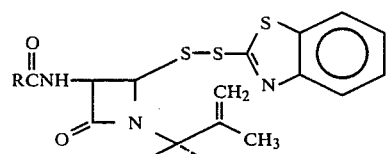

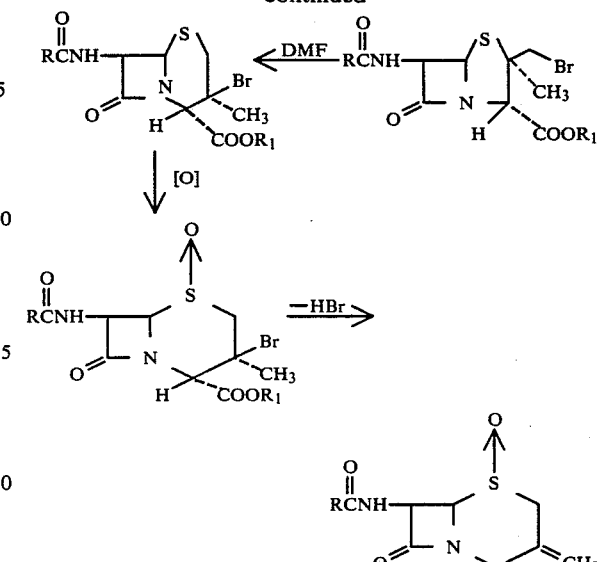

But in this method, the isomerization from 2-halomethylphenam compounds into 3-halomethyl cepham compounds does not proceed completely and 2-halomethylphenam compounds remain as a byproduct. Also there are difficulties in reducing 3-methylene cepham sulfoxide compounds.

DETAILED DESCRIPTION OF THE INVENTION

The method of the present invention, different from the known methods, does not include a reduction step, because 3-methylene cepham compounds are prepared through 3-halomethylbutenoate derivatives of thiazolinoazetidinone of the formula (II). Also this method removes difficulties arising in the photo-chemical reaction.

In the present invention, 3-methylbutenoate derivatives of thiazolinoazetidinone described in the following formula (IV) are halogenated to prepare 3-halomethylbutenoate derivatives of thiazolinoazetidinone of the formula (II). 3-Halomethylbutenoate derivatives of thiazolinoazetidinone of the formula (II) are hydrolyzed by treatment with an aqueous acid solution, the cepham ring then formed and 3-methylene cepham compounds of the formula (I) are obtained. The present invention introduces a great advantage because it can proceeded without any need to separate as an intermediate 4-mercapto azetidinone derivatives represented by the following formula (VI) formed through the hydrolyzing step.

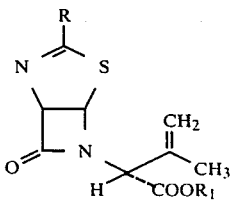
(IV)

Wherein;
R is benzyl or phenoxymethyl,

R₁ is a carboxylic acid protecting group such as benzhydryl, p-nitrobenzyl, benzyl, p-methoxybenzyl, 2,2,2-trichloroethyl, etc.

The method of the present invention is as follows:

(1) The method of preparation of 3-methylbutenoate derivatives of thiazolinoazetidinone (IV) By reacting penicilline sulfoxide esters which have the following formula (V),

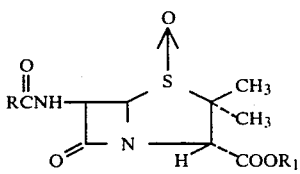 (V)

Wherein;

R is benzyl or phenoxymethyl,

R₁ is a carboxylic acid protecting group such as benzhydryl, p-nitrobenzyl, benzyl, p-methoxybenzyl, 2,2,2-trichloroethyl, etc.

With about 1.1 equivalent of trimethyl phosphine or triethyl phosphine in an anhydrous inert solvent; 3-methylbutenoate derivatives of thiazolinoazetidinone of the formula (IV) can be prepared (refer to U.S. Pat. No. 3,705,892). The solvents which can be used in the aforementioned reaction must have boiling points higher than the reaction temperature. Exemplary of the usable solvents are aromatic hydrocarbons such as benzene, toluene, ethylbenzene, cumene, xylene, etc., halogenated hydrocarbons such as carbon tetrachloride, chloroform, 1,1,2-trichloroethane, etc., are aromatic ethers such as anisol, dimethylether, etc. The most desirable solvents are toluene or xylene. While the reaction proceeds at a temperature of between 75° C. to 175° C. depending on the C₆ substituent, the preferred temperature lies between 110° C. to 155° C.

(2) The method of preparation of 3-halomethylbutenoate derivatives of thiazolinoazetidinone (II)

3-Methylbutenoate derivatives of thiazolinoazetidinone of the formula (IV) are halogenated to obtain 3-halomethylbutenoate derivatives of thiazolinoazetidinone of the formula (II).

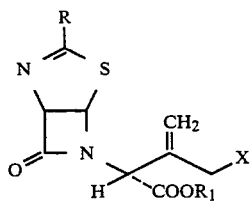 (II)

Wherein;

R is benzyl or phenoxymethyl,

R₁ is a carboxylic acid protecting group such as benzhydryl, p-nitrobenzyl, benzyl, p-methoxybenzyl, 2,2,2-trichloroethyl, X is a halogene such as chloro, bromo, iodo.

The method of halogenation of 3-methylbutenoate derivatives of thiazolinoazetidinone of the formula (IV) was described in U.S. Pat. No. 4,077,970 and British Pat. Nos. 1,472,863 through 1,472,870. In this halogenation, 3-butenoate is transformed into 2-butenoate by isomerization. It was reported in GB 2,048,269A. that the halogenation reaction proceeds at room temperature with an economic yield. The reagent used in the chlorination is such as chlorine molecular t-butylhypochlorite, etc. The desirable solvents in this case are alkyl esters such as methylformate, methylacetate, ethylformate, etc., and they are more useful because they contain a small quantity of carboxylic acid which is sufficient to act as an initiator.

(3) The method of preparation of 3-methylene cepham compounds (I)

In the present invention, 3-methylene cepham compounds of the formula (I) are obtained by treating 3-halomethylbutenoate derivatives of thiazolinoazetidinone of the formula (II) with an aqueous acid solution. The 3-halomethylbutenoate derivatives of thiazolinoazetidinone of the formula (II) have a tendency to be cyclized spontaneously and 3-methylene cepham compounds of the formula (I) can be separated with a good yield. 3-Halomethylbutenoate derivatives of thiazolinoazetidinone of the formula (II) are hydrolyzed with the addition of an aqueous acid solution, and after that, thiazoline rings are opened and 4-mercapto azetidinone derivatives of the formula (VI) are formed in the reaction solution. 4-Mercapto azetidinone derivatives of the following formula (VI), without any need of being separated, proceed by cyclization to form cepham rings to continuously produce 3-methylene cepham compounds of the formula (I).

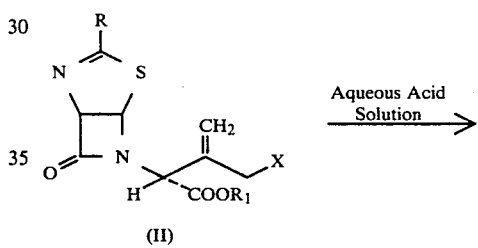

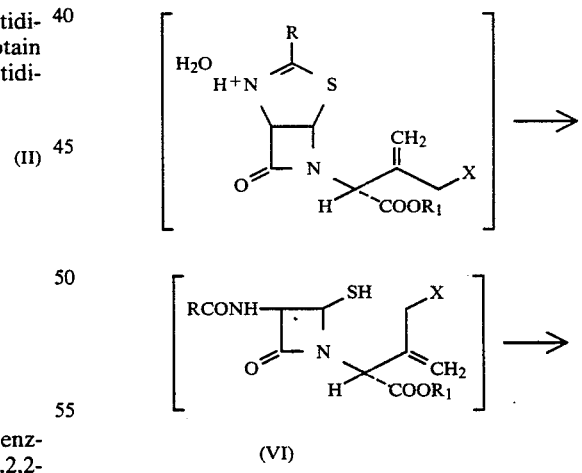

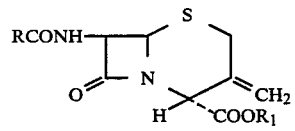

(I)

Wherein;

R is benzyl or phenoxymethyl, $R_1$ is a carboxylic acid protecting group such as benzhydryl, p-nitrobenzyl, benzyl, p-methoxybenzyl, 2,2,2-trichloroethyl, etc.

X is a halogene such as chloro, bromo, iodo, etc.

Acids used in the process of the present invention are inorganic acids such as hydrochloric acid, hydrobromic acid, sulfuric acid, nitric acid, phosphoric acid, perchloric acid, sulfurous acid, etc., or sulfonic acids such as alkyl sulfonic acid, aryl sulfonic acid, etc., or phosphonic acid, carboxylic acid, etc. Solvents used in the reaction are mixed solvents of polar solvents which accelerate the reaction and solvents for dissolving the starting materials. Exemplary of suitable polar solvents are alcohol, carboxylic acid, imide, nitrile, sulfoxide, etc. and examplary of solvents for dissolving the starting material are ester, ether, ketone, or halogenated hydrocarbons. The cyclization reaction of the present invention proceeds rapidly to produce 3-methylene cepham compounds of the formula (I). 3-Halomethylbutenoate derivatives of thiazolinoazetidinone of the formula (II) wherein the halogen substituent is chloro, bromo or iodo produce 3-methylene cepham compounds by treatment with aqueous acid solutions. Of those, iodomethyl is best in reactivity, and when iodomethyl is used, the yield of 3-methylene cepham compounds highly increases because the nucleophilicity increases in the order of chlorine, bromine, iodine. In the conversion from 3-chloromethyl butenoate derivatives of thiazolinoazetidinone of the formula (II) into 3-iodomethylbutenoate derivatives of thiazolinoazetidinone, sodium iodide is used as the known method but about 5 times in excess and anhydrous acetone etc. is used as a solvent. It is desirable that at the early stage of the reaction, the reaction solution is flushed with nitrogen gas to remove oxygen in the solvent and the reaction proceeds under anhydrous condition.

The strong point of the present invention is, as described above, that it can reduce the step of separating 4-mercaptoazetidinone of the formula (VI) and cyclizing by treating it with acid, base or solvents. In an aqueous acid solution, the cyclization reaction to 3-methylene cepham compounds takes place directly and continuously in one reactor, so the reaction proceeds as a one step reaction. Also this method is simple, because the 3-methylene cepham compounds of the formula (I) are obtained directly as the reduced form of 3-methylene cepham sulfoxide compounds.

The following examples are provided to further illustrate the present invention. It is not intended that this invention be limited in scope by reason of any of these examples.

EXAMPLE 1

The method of preparation of p-nitrobenzyl-2-(3-phenoxymethyl-2-thia-6-oxo-4,7-diazabicyclo-[3,2,0]-hept-3-ene-7-yl)-3-chloromethyl-3-butenoate.

3g of p-nitrobenzyl-2-(3-phenoxymethyl-2-thia-6-oxo-4,7-diazabicyclo-[3,2,0]hept-3-ene-7-yl)-3-methyl-3-butenoate was dissolved in 150 ml of methyl formate, 3 ml of propylene oxide was added and then the solution was cooled to 0° to 2° C. with ice water. 1.2 ml of t-butyl hypochlorite was added separately to the solution, in increments with a 5 minute's interval and the solution was stirred at 0° to 2° C. for 1 hour. The solvent was then evaporated in vacuo and the residue was dissolved in 100 ml of dichloromethane. The resulting solution was washed three times with 30 ml of brine water and dried with magnesium sulfate (MgSO$_4$). Evaporation in vacuo of the solvent to dryness gave 2.7 g of light yellow p-nitrobenzyl-2-(3-phenoxymethyl-2-thia-6-oxo-4,7-diazabicyclo -[3,2,0]hept-3-ene-7-yl)-3-chloromethyl-3-butenoate.

m.p.: 105°–107° C.

I.R.: λmax (KBr) 1795, 1787, 1770, 1755, 1740 cm$^{-1}$.

N.M.R.: (CDCl$_3$ δ) 3.95 (s. 2H), 4.94 (s. 2H), 5.18 (s. 1H), 5.23 (s. 1H), 529 (s. 2H), 5.48 (s. 1H), 5.93 (d. 1H. J=4.5 Hz), 6.04 (d. 1H. J=4.5 Hz), 6.88–7.33 (m. 5H), 7.48 (d. 2H. J=9 Hz), 8.23 (d. 2H. J=9 Hz).

EXAMPLE 2

The method of preparation of benzhydryl-2-(3-phenoxymethyl-2-thia-6-oxo-4,7-diazabicyclo-[3,2,0]hept-3-ene-7-yl)-3-chloromethyl-3-butenoate.

3 g of benzhydryl-2-(3-phenoxymethyl-2-thia-6-oxo-4,7-diazabicyclo[3,2,0]hept-3-ene-7-yl)-3- methyl-3-butenoate was dissolved in 75 ml of methylformate, 3 ml of propylene oxide was added and then the solution was cooled to 0° to 2° C. by an icy water. 10.3 ml of t-butylhypochlorite was added three times with 5 minute's interval and the solution was stirred at 0° to 2° C. for 1 hour. The solvent was then evaporated in vacuo at room temperature and the residue was dissolved in 80 ml of dichloro methane. The resulting solution was washed three times with 50 ml of brine water and dried with magnesium sulfate (MgSO$_4$). Evaporation in vacuo of the solvent to dryness gave 2.8 g of light yellow benzhydryl-2-(3-phenoxymethyl-2-thia-6-oxo-4,7-diazabicyclo-[3,2,0]-hept-3-ene-7-yl)-3-chloromethyl-3-butenoate.

N.M.R.: (CDCl$_3$ δ) 3.86 (s. 2H), 4.82 (s. 2H), 4.89 (s. 1H), 5.26 (d. 2H. J=4 Hz), 5.76 (d. 2H. J=4 Hz), 5.90 (d. 2H. 4 Hz), 6.92 (s. 1H), 7.23 (s. 5H).

EXAMPLE 3

The method of preparation of p-nitrobenzyl-2-(3-benzyl-2-thia-6-oxo-4,7-diazabicyclo-[3,2,0]-hept-3-ene-7-yl)-3-chloromethyl-3-butenoate.

0.9 g of p-nitrobenzyl-2-(3-benzyl-2-thia-6-oxo-4,7-diazabicyclo-[3,2,0]-hept-3-ene-7-yl)-3-methyl-3-butenoate was dissolved in 100 ml of methylformate and 11 ml of propylene oxide was added. 0.3 ml of t-butylhypochlorite was added and the solution was stirred at room temperature for 1 hour. The solvent was then evaporated in vacuo and the residue was dissolved in 50 ml of dichloromethane. The resulting solution was washed three times with 20 ml of brine water and was dried with magnesium sulfate (MgSO$_4$). Evaporation in vacuo of the solvent to dryness gave 0.7 g of p-nitrobenzyl-2-(3-benzyl-2-thia-6-oxo-4,7-diazabicyclo-[3,2,0]hept-3-ene-7-yl)-3-chloromethyl-3-butenoate.

N.M.R. (CDCl$_3$,δ) 3.6 (q, J=14 Hz), 3.84 (s), 5.1 (s), 5.25 (s), 5.4 (s), 5.86 (br, s), 7.28 (d, J=8 Hz), 8.16 (d, J=8 Hz).

EXAMPLE 4

By the method analogous to the Example 1, the following compounds were produced.

(1) 2,2,2-trichloroethyl-2-(3-phenoxymethyl-2-thia-6-oxo-4,7-diazabicyclo[3,2,0]hept-3-ene-7-yl)-3-chloromethyl-3-butenoate (2) benzyl-2-(3-phenoxymethyl-2-thia-6-oxo-4,7-diazabicyclo[3,2,0]-hept-3-ene-7-yl)-3-chloromethyl-3-butenoate (3) p-methoxybenzyl-2-(3-phenoxymethyl-2-thia-6-oxo-4,7-diazabicyclo [3,2,0]-hept-3-ene-7-yl)-3-chloromethyl-3-butenoate (4) benzhydryl-2-(3-benzyl-2-thia-6-oxo-4,7-diazabicyclo-[3,2,0]-hept-3-ene-7-yl)-3-chloromethyl-3-butenoate (5) 2,2,2-trichloroethyl-2-(3-benzyl-2-thia-6-oxo-4,7-diazabicyclo[3,2,0]-hept-3-ene-7-yl)-3-chloromethyl-3-butenoate (6) benzyl-2-(3-benzyl-2-thia-6-oxo-4,7-diazabicyclo[3,2,0]-hept-3-ene-7-yl)-3-chloromethyl-3-butenoate (7) p-methoxybenzyl-2-(3-benzyl-2-thia-6-oxo-4,7-diazabicyclo-[3,2,0]hept-3-ene-7-yl)-3-chloromethyl-3-butenoate

EXAMPLE 5

The method of preparation of benzhydryl-2-(3-phenoxymethyl)-2-thia-6-oxo-4,7-diazabicyclo[3,2,0]-hept-3-ene-7-yl)-3-iodomethyl-3-butenoate 3 g of benzhydryl-2-(3-phenoxymethyl-2-thia-6-oxo-4,7-diazabicyclo[3,2,0]hept-3-ene-7-yl)-3-chloromethyl-3-butenoate was put into the solution in which 4.2 g of sodium iodide was dissolved in 15 ml of aceton. The solution was flushed with nitrogen gas to remove oxygen contained in the solvent and was stirred under nitrogen atmosphere for about 12 hours. The solvent was removed under vacuum and 120 ml of dichloromethane was added. The solution was then washed three times with 50 ml of brine water and was dried with magnesium sulfate (MgSO$_4$). Evaporation of the solvent to dryness gave 3.1 g of benzhydryl-2-(3-phenoxymethyl-2-thia-6-oxo-4,7-diazabicyclo[3,2,0]-hept-3-ene-7-yl)-3-iodomethyl-3-butenoate.

N.M.R. (CDCl$_3$, δ) 3.88 (s, 2H), 4.87 (s, 2H), 4.93 (s. 1H), 5.32 (d. 2H, J=4 Hz), 5.82 (d, 2H, J=4.5 Hz), 5.98 (d, 2H, J=4.5 Hz), 6.90 (s, 1H), 7.30 (s, 5H).

EXAMPLE 6

The method of preparation of p-nitrobenzyl-2-(3-phenoxymethyl-2-thia-6-oxo-4,7-diazabicyclo[3,2,0-]hept-3-ene-7-yl)-3-iodomethyl-3-butenoate.

2 g of p-nitrobenzyl-2-(3-phenoxymethyl-2-thia-6-oxo-4,7-diazabicyclo[3,2,0]hept-3-ene-7-yl)-3-chloromethyl-3-butenoate was dissolved in 10 ml of acetone and this solution was put into 15 ml of aceton solution dissolving 3 g of sodium iodide. The resulting solution was flushed with nitrogen gas to remove oxygen contained in the solvent and was stirred under nitrogen atmosphere for about 12 hours. The solvent was removed under vacuum and 100 ml of dichloromethane was added. The solution was then washed three times with 50 ml of brine water and it became clear. Drying with magnesium sulfate (MgSO$_4$) and evaporation of the solvent to dryness gave 2 g of p-nitrobenzyl-2-(3-phenoxymethyl-2-thia-6-oxo-4,7-diazabicyclo[3,2,0]-hept-3-ene-7-yl)-3-iodomethyl-3-butenoate as a crystal.

N.M.R. (CDCl$_3$, δ) 3.89 (s, 2H), 4.88 (s, 2H), 5.12 (s, 1H), 5.17 (s, 1H), 5.23 (s, 1H), 5.42 (s, 1H), 5.87 (d, 1H, J=4.5 Hz), 5.97 (d, 1H, J=4.5 Hz), 6.80–7.31 (m, 5H), 7.4 (d, 2H, J=9 Hz).

EXAMPLE 7

By the method described in the Example 5, the following compounds were produced.

(1) 2,2,2-trichloroethyl-2-(3-phenoxymethyl-2-thia-6-oxo-4,7-diazabicyclo[3,2,0]hept-3-ene-7-yl)-3-iodomethyl-3-butenoate (2) benzyl-2-(3-phenoxymethyl-2-thia-6-oxo-4,7-diazabicyclo[3,2,0]-hept-3-ene-7-yl)-3-iodomethyl-3-butenoate (3) P-methoxybenzyl-2-(3-phenoxymethyl-2-thia-6-oxo-4,7-diazabicyclo[3,2,0]hept-3-ene-7-yl)-3-iodomethyl-3-butenoate (4) p-nitrobenzyl-2-(3-benzyl-2-thia-6-oxo-4,7-diazabicyclo[3,2,0]hept-3-ene-7-yl)-3-iodomethyl-3-butenoate (5) benzhydryl-2-(3-benzyl-2-thia-6-oxo-4,7-diazabicyclo[3,2,0]hept-3-ene-7-yl)-3-iodomethyl-3-butenoate (6) 2,2,2-trichloroethyl-2-(3-benzyl-2-thia-6-oxo-4,7-diazabicyclo[3,2,0]hept-3-ene-7-yl)-3-iodomethyl-3-butenoate (7) benzyl-2-(3-benzyl-2-thia-6-oxo-4,7-diazabicyclo-[3,2,0]hept-3-ene-7-yl)-3-iodomethyl- 3-butenoate (8) p-methoxybenzyl-2-(3-benzyl-2-thia-6-oxo-4,7-diazabicyclo-[3,2,0]hept-3-ene-7-yl)-3-iodomethyl-3-butenoate

EXAMPLE 8

The method of preparation of benzhydryl-3-methylene-8-oxo-7-phenoxyacetamido-5-thia-1-azabicyclo[4,2,0]octane-2-carboxylate 1.4 g of benzhydryl-2-(3-phenoxymethyl-2-thia-6-oxo-4,7-diazabicyclo[3,2,0]hept-3-ene-7-yl)-3-iodomethyl-3-butenoate was dissolved in a mixed solution containing 28 ml of dichloromethane, 28 ml of acetone and 6.59 ml of 30% perchloric acid. The resulting solution was stirred for 2 hours at room temperature and was diluted with water. After organic solvent layer was separated, water layer was extracted by dichloromethane and combined with the organic solvent layer separated previously. Then the solution was washed two times with brine water and dried with magnesium sulfate (MgSO$_4$). Evaporation in vacuo of the solvent to dryness and purification by silica gel column (eluent as hexane: aceton=5:1) gave 0.74 g of the above compound as a crystal.

I.R. (λmax, KBr, cm$^{-1}$): 1775, 1740, 1685, 1595, 1520, 1490.

N.M.R. (DMSO-d$_6$,δ): 3.45 (br, s, 2H), 4.60 (s, 2H), 5.25 (d. J=4.5 Hz, 1H), 5.34, 5.41 (2s, 2H), 5.48 (s, 1H) 5.53 (d, J=8.5 & 4.5 Hz, 1H), 6.84 (s, 1H), 6.90–7.50 (m, 15H), 9.06 (d, J=8.5 Hz, 1H).

EXAMPLE 9

The method of preparation of benzhydryl-3-methylene-8-oxo-7-phenylacetamido-5-thia-1-azabicyclo[4,2,-0]octane-2-carboxylate By the method analogous to the Example 8, benzhydryl-3-methylene-8-oxo-7-phenylacetamido-5-thia-1-azabicyclo[4,2,0]-octane-2-carboxylate was obtained by the use of benzhydryl-2-(3-benzyl-2-thia-6-oxo-4,7-diazabicyclo[3,2,0]-hept-3-ene-7-yl)-3-iodomethyl-3-butenoate.

m.p.: 143°–146° C.

N.M.R. (CDCl$_3$, δ): 3.04 (ABq, J=14 Hz, 2H), 4.8–5.3 (m, 3H), 6.71 (s, 1H), 7.0–7.8 (m, 15H).

EXAMPLE 10

The method of preparation of benzhydryl-3-methylene-8-oxo-7-phenoxyacetamido-5-thia-1-azabicyclo[4,2,0]octane-2-carboxylate 2 g of benzhydryl-2-(3-phenoxymethyl-2-thia-6-oxo-4,7-diazabicyclo[3,2,0]hept-3-ene-7-yl)-3-chloromethyl-3-butenoate was dissolved in a mixed solution containing 40 ml of dichloromethane, 40 ml of acetone and 11 ml of 30% perchloric acid. The resulting solution was stirred for 1 hour at room temperature, diluted with water and extracted by dichloromethane. The extract was washed with brine water and was dried with magnesium sulfate (MgSO$_4$). Evaporation in vacuo of the solvent to dryness gave 0.73 g of the above compound as a crystal. The analysis data were the same as in the Example 8.

EXAMPLE 11

The method of preparation of p-nitrobenzyl-3-methylene-8-oxo-7-phenoxyacetamido-5-thia-1-azabicyclo[4,2,0]octane-2-carboxylate.

2g of p-nitrobenzyl-2-(3-phenoxymethyl-2-thia-6-oxo-4,7-diazabicyclo[3,2,0]hept-3-ene-7-yl)-3-iodomethyl-3-butenoate was dissolved in a mixed solution containing 40 ml of dichloromethane, 40 ml of acetone and 9 ml of 30% perchloric acid. The resulting solution was stirred for 2 hours at room temperature, and diluted with water and extracted by dichloromethane. The extract was washed twice with brine water and dried with magnesium sulfate (MgSO$_4$). Evaporation in vacuo of the solvent to dryness gave 1.02 g of p-nitrobenzyl-3-methylene-8-oxo-7-phenoxyacetamido-5-thia-1-azabicyclo[4,2,0]octane-2-carboxylate.

m.p.: 84°–94° C.

N.M.R. (CDCl$_3$, δ): 3.42 (ABq, 2H), 4.53 (s, 2H), 5.20–5.50 (m, 6H), 5.75 (q, 1H), 6.80–8.35 (m, 10H).

I.R. (λmax, KBr, cm$^{-1}$): 1770, 1755, 1675, 1595, 1515, 1490.

EXAMPLE 12

The method of preparation of p-nitrobenzyl-3-methylene-8-oxo-7-phenylacetamido-5-thia-1-azabicyclo[4,2,-0]octane-2-carboxylate. By the method described in the Example 11, p-nitrobenzyl-3-methylene-8-oxo-7-phenylacetamido-5-thia-1-azabicyclo[4,2,0]octane-2-carboxylate was obtained by the use of p-nitrobenzyl-2-(3-benzyl-2-thia-6-oxo-4,7-diazabicyclo[3,2,0]hept-3-ene-7-yl)-3-iodomethyl-3-butenoate.

I.R. (λmax, KBr, cm$^{-1}$): 1770, 1765, 1670.

N.M.R. (CDCl$_2$, δ): 3.15 (ABq, J=14 Hz, 2H), 3.68 (s, 2H), 5.15 & 5.47 (Br, s, 2H).

EXAMPLE 13

The method of preparation of p-nitrobenzyl-3-methylene-8-oxo-7-phenoxyacetamido-5-thia-1-azabicyclo[4,2,0]octane-2-carboxylate.

1.9 g of p-nitrobenyl-2-(3-phenoxymethyl-2-thia-6-oxo-4,7-diazabicyclo[3,2,0]hept-3-ene-7-yl)-3-chloromethyl-3-butenoate was dissolved in a mixed solution containing 38 ml of dichloromethane, 38 ml of acetone and 11 ml of 30% perchloric acid. The resulting solution was stirred for 1 hour at room temperature, diluted with water and extracted by dichloromethane. The extract was washed with brine water and was dried with magnesium sulfate (MgSO$_4$). Evaporation in vacuo of the solvent to dryness gave 6.58 g of the above compound as a crystal. The analysis data were the same as in the Example 11.

EXAMPLE 14

The method of preparation of 2,2,2-trichloromethyl-3-methylene-8-oxo-7-phenylacetamido-5-thia-1-azabicyclo[4,2,0]octane-2-carboxylate. By the same method as in the Example 8, 2,2,2-trichloroethyl-3-methylen-8-oxo-7-phenylacetamido-5-thia-1-azabicyclo[4,2,0]octane-2-carboxylate was obtained by the use of 2,2,2-trichloroethyl-2-(3-benzyl-2-thia-6-oxo-4,7-diazabicyclo[3,2,0]hept-3-ene-7-yl)-3-iodomethyl-3-butenoate.

m.p.: 149°–152° C.

I.R. (λmax, KBr, cm$^{-1}$): 1765, 1760, 1670.

N.M.R. (CDCl$_3$, δ): 3.18 & 3.66 (ABq, 2H, J=14 Hz), 5.14 & 5.26 (br, s, 2H).

EXAMPLE 15

The method of preparation of p-methoxybenzyl-3-methylene-8-oxo-7-phenoxyacetamido-5-thia-1-azabicyclo[4,2,0]octane-2-carboxylate.

By the method described in the Example 11, p-methoxybenzyl-3-methylene-8-oxo-7-phenoxyacetamido-5-thia-1-azabicyclo[4,2,0]octane-2-carboxylate was obtained by the use of p-methoxybenzyl-2-(3-phenoxymethyl-2-thia-6-oxo-4,7-diazabicyclo[3,2,0-]hept-3-ene-7-yl) -3-iodomethyl-3-butenoate.

m.p.: 108°–109° C.

N.M.R. (CDCl$_3$, δ): 3.34 (ABq, 2H), 3.79 (s, 3H), 4.50 (s, 2H), 5.08–5.50 (m, 6H), 5.65 (q, 1H), 6.95–7.45 (m, 10H).

We claim:

1. A method for the preparation of 3-methylene cepham compounds of the formula (I) comprising reacting 3-halomethyl butenoate derivatives of thiazolinoazetidinone of the formula (II) with an aqueous acid solution in a mixed organic solvent.

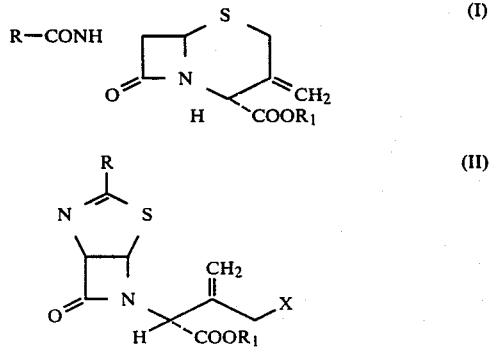

Wherein R is benzyl or phenoxymethyl, R$_1$ is a carboxylic acid protecting group and X is halogen.

2. A method according to claim 1, wherein R$_1$ is a member selected from the group consisting of benzhydryl, p-nitrobenzyl, benzyl, p-methoxybenzyl, or 2,2,2-trichloroethyl.

3. A method according to claim 1 wherein R$_1$ is a member selected from the group consisting of benzhydryl, p-nitrobenzyl, benzyl, p-ethoxybenzyl, 2,2,2-trichloroethyl, and X is chlorine, bromine, or iodine.

4. A method according to claim 1, wherein said mixed organic solvent is comprised of solvents selected from the group consisting of alcohol, acetone, dichloro methane and tetrahydrofuran.

5. A method according to claim 1 wherein said aqueous acid solution is comprised of an inorganic acid selected from the group consisting of hydrochloric acid, hydrobromic acid, sulfuric acid, nitric acid, perchloric acid, sulfurous acid, alkyl sulfonic acid, arylsulfonic acid, phosphonic acid and carboxylic acid.

6. A method according to claim 1 wherein 5 to 10 moles of an acid is used with 1 mole of 3-halomethyl-butenoate derivatives of thiazolinoazetidinone of the formula (II).

7. A method according to claim 1, wherein the reaction medium is flushed with nitrogen gas to remove oxygen from the solvent.

8. A method according to claim 3, wherein X is iodine.

9. A method for the preparation of 3-methylene cepham compounds of the formula (I).

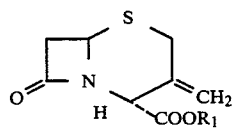
(I)

wherein R is benzyl or phenoxymethyl and $R_1$ is a carboxylic acid protecting group, comprising reacting 3-halomethyl butenoate derivatives of thiazolinoazetidinone of the formula II

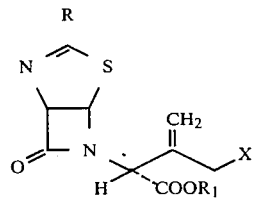
(II)

wherein R and $R_1$, are as defined above and X is halogen, with an acid in a mixed polar organic solvent under anhydrous conditions, said acid being a member selected from the group consisting of hydrochloric acid, hydrobromic acid, sulfuric acid, nitric acid, perchloric acid, sulfurous acid, alkyl sulfonic acid, arylsulfonic acid, phosphonic acid and carboxylic acid, said organic solvent being a member selected from the group consisting of alcohol, acetone, dichloro methane and tetrahydrofuran, and wherein the reaction medium is flushed with nitrogen gas to remove oxygen from the solvent.

10. A method according to claim 9, wherein $R_1$ is a member selected from the group consisting of benzhydryl, p-nitrobenzyl, benzyl, p-methoxybenzyl, or 2,2,2-trichloroethyl.

11. A method according to claim 9, wherein $R_1$ is a member selected from the group consisting of benzhydryl, p-nitrobenzyl, benzyl, p-ethoxybenzyl, 2,2,2-trichloroethyl, and X is chlorine, bromine or iodine.

12. A method according to claim 11, wherein X is iodine.

* * * * *